United States Patent
Lorenz et al.

(10) Patent No.: US 9,783,671 B2
(45) Date of Patent: Oct. 10, 2017

(54) CROSS-LINKED PLASTIC MATERIAL WITH AN INTRINSIC ANTIMICROBIAL EFFECT BASED ON UNSATURATED POLYESTERS

(71) Applicant: FACHHOCHSCHULE MÜNSTER, Steinfurt (DE)

(72) Inventors: Reinhard Lorenz, Steinfurt (DE); Björn Fischer, Saerbeck (DE); Martin Kreyenschmidt, Lohne (DE); Judith Kreyenschmidt, Rheinbach (DE)

(73) Assignee: Fachhochschule Münster, Steinfurt (DE)

( * ) Notice: Subject to any disclaimer, the term of this patent is extended or adjusted under 35 U.S.C. 154(b) by 39 days.

(21) Appl. No.: 14/764,621

(22) PCT Filed: Jan. 31, 2014

(86) PCT No.: PCT/EP2014/051880
§ 371 (c)(1),
(2) Date: Jul. 30, 2015

(87) PCT Pub. No.: WO2014/118314
PCT Pub. Date: Aug. 7, 2014

(65) Prior Publication Data
US 2015/0361259 A1    Dec. 17, 2015

(30) Foreign Application Priority Data
Jan. 31, 2013  (EP) .................................... 13000472

(51) Int. Cl.
*C08L 67/06* (2006.01)
*C07C 209/08* (2006.01)
*C09D 5/14* (2006.01)
*C07C 211/28* (2006.01)
*C07C 211/27* (2006.01)

(52) U.S. Cl.
CPC ............ *C08L 67/06* (2013.01); *C07C 209/08* (2013.01); *C07C 211/27* (2013.01); *C07C 211/28* (2013.01); *C09D 5/14* (2013.01)

(58) Field of Classification Search
USPC ...................................... 523/122, 500; 564/1
See application file for complete search history.

(56) References Cited

U.S. PATENT DOCUMENTS

| | | | |
|---|---|---|---|
| 3,274,294 A * | 9/1966 | Stanton | C08F 283/00 522/136 |
| 3,385,909 A * | 5/1968 | Haag, Jr. | C08L 75/04 525/128 |
| 4,021,416 A | 5/1977 | Locatell, Jr. | |
| 4,447,580 A | 5/1984 | Ai et al. | |
| 4,810,567 A | 3/1989 | Calcaterra et al. | |
| 5,614,568 A | 3/1997 | Mawatari et al. | |
| 6,200,680 B1 | 3/2001 | Takeda et al. | |
| 6,242,526 B1 | 6/2001 | Siddiqui et al. | |
| 6,297,314 B1 | 10/2001 | Hintze-Brüning et al. | |
| 7,563,734 B2 * | 7/2009 | Gleason | A61L 15/24 424/443 |
| 2005/0069967 A1* | 3/2005 | Sumida | G01N 33/54313 435/7.92 |
| 2005/0079150 A1* | 4/2005 | Gellman | A61K 31/74 424/78.27 |
| 2010/0247889 A1 | 9/2010 | Kliesch et al. | |

FOREIGN PATENT DOCUMENTS

| | | |
|---|---|---|
| DE | 44 32 985 A1 | 3/1996 |
| JP | 2000 239 281 A | 9/2000 |
| WO | 2004/033568 A1 | 4/2004 |

OTHER PUBLICATIONS

Martin et al, Initiated chemical vapor deposition of antimicrobial polymer coatings, Biomaterials 28 (2007), 909-915, Elsevier.*

* cited by examiner

*Primary Examiner* — Tae H Yoon
(74) *Attorney, Agent, or Firm* — Jason D. Voight

(57) ABSTRACT

The present invention relates to a radically curable chemical composition in the form of a resin for the production of materials with an intrinsically antimicrobial effect, as well as a process for the production of such resins and materials, as well as the use of an amino-functionalized styrene derivative as reactive diluents. The cross-linked plastic formed upon curing has an intrinsically antimicrobial effect without the use of additional biocides.

15 Claims, No Drawings

CROSS-LINKED PLASTIC MATERIAL WITH AN INTRINSIC ANTIMICROBIAL EFFECT BASED ON UNSATURATED POLYESTERS

This is the national stage of International Application PCT/EP2014/051880, filed Jan. 31, 2014. This application claims priority to European Application EP 13000472.4, filed Jan. 31, 2013.

The present invention relates to a radically curable chemical composition in the form of a resin for the production of materials with an intrinsically antimicrobial effect, and the application of such materials, as well as a process for the production of such resins and materials, as well as the use of amino-functionalized styrene derivatives as reactive diluents.

Growth of algae, fungi or mussels is an unwanted side effect of many plastic and material applications. The formation of bacterial biofilms and the transmission of pathogens can cause considerably more severe problems, however. Fighting and avoiding such unwanted effects is therefore of great medical, hygienic, food technological and practical importance: The issue is generally managed by mechanical-chemical purification, by adding classical biocides (e.g. silver, copper or zinc compounds or organic compounds such as triclosan, 10,10"-oxybisphenoxyarsine, N-(trifluoromethylthio)phthalimide, N-(trichloromethylthio)-phthalimide, various isothiazolinones) to the plastic or coating, or by continuous use of various external disinfectants—as is the case in hospitals or in the food and meat processing industry, for example.

Until now, equipping surfaces with antimicrobial properties, without the added antimicrobial active agent diffusing from the surface, has been difficult. There have been some experiments on the use of antimicrobial functionalized monomers for the synthesis of antimicrobial polymers. One such monomer was, for example, tert-butylaminoethyl methacrylate (TBAEMA). The disadvantage of these polymers available until now, such as poly(TBAEMA) was that their glass transition temperature is very low, for poly (TBAEMA), for instance, it is below 50° C.

U.S. Pat. No. 6,242,526 describes antimicrobial polymer latexes derived from an ethylenically unsaturated acid as anion, and quaternary ammonium compounds as cation, with the antimicrobial effect being attributable to the quaternary ammonium compounds.

U.S. Pat. No. 4,810,567 describes antimicrobial fabrics, wherein various base fabrics are functionalized from a graft copolymerization of monomers containing acid groups, which are bound to antimicrobial proteins and antibiotics through amidation.

U.S. Pat. No. 5,614,568 describes an antibacterial thermoplastic compound containing silver, copper or zinc zeolites, amongst other things. It uses polymeric and low-molecular additives with special functional groups to increase the antibacterial effect.

U.S. Pat. No. 4,447,580 describes a co-polymer based on acrylate containing amino-functionalized styrene monomer units for the production of forming coatings for cataphoresis. These co-polymers are synthesized through a thermally activated Michael addition reaction with oligomeric and polymeric compounds containing activated double bonds. The amino-functionalized styrene derivatives are neither used for radical cross-linking nor for an antimicrobial effect.

JP 2000 239 281 A describes the synthesis of amino-functionalized styrene derivatives, from which cross-linked polymers are produced, which are then converted into immobilized polymeric lithium amides. They are used for organic synthesis.

U.S. Pat. No. 6,200,680 describes a process for producing zinc oxide fine particles using polymeric agents, such as amino-functionalized polymers based on amino-functionalized styrene derivatives.

U.S. Pat. No. 4,021,416 describes aminoethanethiol-functionalized styrene derivatives which can be used as complexing agents for silver ions and/or soluble silver complexes in photography.

Kuno et al. (Reactive & Functional Polymers 43 (2000) 43-51) describe poly[N-(p-vinylbenzyliden)-tert-butylaminoxide] as new radical trapping for applications in environmental technology.

DE 102 42 561 A1 discloses an antimicrobial coating containing polymers of special cyclic amines with at least one polymerizable unsaturated group. Further, a process for the production of such antimicrobial coatings and their use in the production of products having antimicrobial characteristics is described.

DE 44 32 985 A1 discloses binding agents and their production, as well as their use as coating agents for scratch- and acid-resistant coatings. The binding agents are synthesized through radical polymerization of a) (meth)acrylic monomers and, if necessary, further radical polymerizable monomer(s) in the presence of b) cyclo-olefin-homo-polymers and/or cyclo-olefin-co-polymers, which are free from olefinic double bonds.

DE 197 23 504 C1 discloses a coating agent, in particular for coating plastics, processes for its production and its use as topcoat enamel or varnish. The coating agents contain
a) one or more special polyester resins,
b) one or more special polyacrylate resins,
c) one or more di- and/or poly-isocyanates
d) one or more light stabilizers based on an UV absorber
e) one or more special light stabilizers based on sterically hindered amines, and
f) one or more organic solvents.

In his article "Schutzschicht gegen Bakterien" (Nachrichten aus der Chemie, 59, November 2011, p. 1039-43), H. Menzel offers an overview of antimicrobial coatings based on polymers with hydrophobic structural elements in combination with high positive charge density which are suitable for medical applications. The various mechanisms with regard to gram-positive and gram-negative bacteria are briefly described. Most structures are based on quaternary ammonia and phosphonium ions. Antimicrobial polymers for compact material applications are not addressed.

The object of the present invention is to provide a technology which can easily be applied in practice, for the production of antimicrobial surfaces and products, from which no antimicrobial additive will diffuse out of the surface or the product. Another object consist of the provision of an antimicrobial material, which has been antimicrobially functionalized in the bulk, and which will thus still be antimicrobial when the surface has been damaged or changed, for example through impact, abrasion or cut, forming a new surface.

In the first embodiment, the object underlying the invention is based is solved by a UP resin composition for the production of products with antimicrobial effect.
a) an unsaturated polyester from dicarboxylic acid and/or anhydride on the one hand, and diol with a molar ratio of 1.25:1 to 0.75:1 on the other hand, with dicarboxylic acid and/or the anhydride having been at least partially functionalized with a radically reactive double bond, and b) styrene derivative as reactive diluent, with the UP resin composition preferably containing 0.5 to 8 styrene derivative molecules in each double bond in component a), and with at least one entity having been amino-functionalized from styrene derivative, dicarboxylic acid and/or diol selectively, with the equation for the amino-functionality being

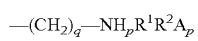

with
q being either 0, 1 or 2, with q≠0, provided the functionality is bound to an aromatic,
p being 0 or 1,
$R^1$ having been selected from H, linear or branched or cyclic alkyl residues with 1 to 10 carbon atoms,
$R^2$ being a linear or branched or cyclic alkyl residue with 1 to 10 carbon atoms,
A being the anion of an acid, and
the amine nitrogen N of the above formula being neutral (p=0) or positively (p=1) charged.

The cross-linked plastic material formed upon curing of this UP resin composition in accordance with the present invention has an intrinsically antimicrobial effect without the use of additional biocides. The new materials are therefore referred to as intrinsically antimicrobial. The advantage of the UP resin composition in accordance with the present invention is that it allows the production of products from which antimicrobial active agents cannot diffuse, and that these products remain antimicrobial even upon mechanical changes or damage to the surface.

The UP resin composition within the meaning of the invention contains one unsaturated polyester and at least one reactive diluent.

It has been shown that the task at the basis of the invention can be solved with radical cross-linking resins of the unsaturated polyester resin-type (UP resins). The reactive diluent which is generally used, styrene, is replaced by an amino-functionalized styrene derivative, a mixture of various amino-functionalized styrene derivatives, a mixture of one or more amino-functionalized styrene derivatives with one or more amino-functionalized methacrylate(s) or one of these mixtures with further reactive diluents. Further reactive diluents are, for example, styrene, methylstyrene, vinyl toluene, tert-butylstyrene, 4-vinylpyridine, 3-vinylpyridine, 2-vinylpyridine, methylmethacrylate, divinylbenzene, 1,2,4-trivinylcyclohexane, diallyl phthalate, diallyl isophthalate, triallyl isocyanurate.

Additionally or alternatively, the unsaturated polyester can be antimicrobially functionalized in UP resin with alkylamino or dialkylamino groups. Furthermore, mixtures of these antimicrobially equipped UP resins with intrinsically antimicrobial VE (vinylester) and/or VEU (vinylester urethane) resins is possible in accordance with the present invention.

Furthermore, mixtures of thermoplastic polymers and intrinsically antimicrobial thermoplastic polymers are possible according to the present invention, for example for impact modification or shrinkage compensation of the resulting thermosets. Mixtures of these antimicrobially equipped UP resins with conventional, non-microbially equipped resins of the UP resin, VE resin, VEU resin and methacrylate resin-types are possible in accordance with the present invention, as long as the antimicrobial effect remains intact.

Unsaturated Polyester

Unsaturated polyester, which is often solid or semi-solid at room temperature, is produced by polycondensation in the melt of dicarboxylic acids and anhydrides, for example, which have at least partially been functionalized with a radically reactive double bond, and of diols. Mixing the unsaturated polyester with the reactive diluent produces a resin which is usually liquid at room temperature and which is referred to as unsaturated polyester resin (UP resin). After radically curing (chemically cross-linking) the UP resin, the product is referred to as UP thermoset or UP network.

After polycondensation of dicarboxylic acid and/or anhydride on the one hand, and diol on the other hand, unsaturated polyester is present as a mixture of polymer, oligomer and residual monomer according to the respective molar mass distribution.

Dicarboxylic acid, anhydride and diol within the meaning of the invention can also be mixtures of various dicarboxylic acids, anhydrides and diols.

The molar ratio between dicarboxylic acid and/or anhydride one the one hand and diol on the other hand is preferably in the range between 0.9:1 and 1:0.9, particularly preferably between 1.03:1 and 0.97:1, in order to create unsaturated polyester with sufficient molar mass. Furthermore, any side reactions which may lead to the formation of volatile side products can have a strong effect on the necessary stoichiometry. This could be the formation of tetrahydrofuran when using butane-1,4-diol; or the formation of 2-ethyl-4-methyl-1,3-dioxolane when using 1,2-propylene glycol. Both side reactions can lead to a clear excess becoming necessary for condensation. In the case of 1,2-propylene glycol, this is preferably 7-15 mol %, in the case of butane-1,4-diol it is preferably around 30 mol %.

Dicarboxylic acids, for example, can be divided into two types:
radically reactive carboxylic acids, in particular citraconic acid, fumaric acid, itaconic acid, maleic acid and/or mesaconic acid, which enable the radical cross-linking of the unsaturated polyester with the reactive diluent following polycondensation.
non-reactive dicarboxylic acids are only involved in the polycondensation reaction, but not in the cross-linking reaction. These include aromatic dicarboxylic acids (phthalic acid, isophthalic acid, terephthalic acid, etc.), aliphatic dicarboxylic acids (succinic acid, adipic acid, sebacic acid, etc.) as well as cycloaliphatic dicarboxylic acids (1,2-cyclohexandicarboxylic acid, 1,4-cyclohexandicarboxylic acid, 1,2,5,6 tetrahydrophthalic acid, etc.)

The anhydride may be an anhydride of the above-mentioned dicarboxylic acids. The mixture of dicarboxylic acids may contain up to 10% of a tricarboxylic acid or a tetracarbonic acid, e.g. trimellitic acid or trimellitic acid anhydride, or pyromellitic acid or pyromellitic acid dianhydride.

The diol is preferably selected from the group of 1,2-ethylene glycol, propane-1,2-diol, propane-1,3-diol, diethylene glycol, dipropylene glycol, triethylene glycol, tripropylene glycol, neopentyl glycol, butane-1,3-diol, butane-1,2-diol, butane-2,3-diol, butane-1,4-diol, 2-butyl-2-ethyl-1,3-propanediol, 2-methyl-1,3-propanediol, pentane-1,5-diol, 1,6-hexandiol, 2,4-dimethyl-2-ethylhexan-1,3-diol, hydroxypivalic acid neopentylglycolester, isosorbide, cycloaliphatic diol (tricyclodecandimethanol, perhydrogenated bisphenol A, 1,4-cyclohexandimethanol, norbornene glycol, etc.), ethoxylated and propoxylated bisphenol A or mixtures thereof.

Within the meaning of the invention, diol can also be a mixture of various diols containing one triol up to a maximum of 10 mol %. Triol is preferably selected from glycerine, trimethylolpropane, triethanolamine, triisopropanolamine or mixtures thereof. Instead of triol, another trifunctional compound may also be used, such as dimethylol butyric acid or dimethylolpropionic acid.

Dicyclopentadiene can be converted with maleic acid to monofunctional dicyclopentadienyl-maleic acid semi-ester, which can be inserted into unsaturated polyesters in limited amounts. According to the invention, these (so-called DCPD resins) can also be functionalized antimicrobially.

Reactive Diluent

Within the meaning of the invention, in this context both a single, suitable monomer and a suitable monomer mixture may be referred to as reactive diluent. The decisive factor is that the monomer or the monomer mixture allows radical cross-linking and are inserted fully or largely into the network.

Apart from styrene derivative, the composition may contain b) one or several further reactive diluents from the group of styrene derivatives and/or methacrylates and/or higher functional monomers.

The ratio of double bonds in component a) and styrene derivative molecule is generally not limited. In a preferred embodiment, for each double bond in component a) 0.5 to 8, preferably 0.7 to 7, more preferably 1 to 6, even more preferably 1.5 to 4, in particular 2.0 to 3.5 styrene derivative molecules are contained in the composition. If the number is below this, the viscosity of the composition may be too high, or the cross-linking may not be sufficient. If the number is above this, the viscosity of the composition may be too low, or the styrene derivative molecules may not react completely and free residual monomer may diffuse out of the product or the surface. To prevent this, the residual monomer content should preferably be reduced by prolonged post-cure at a raised temperature.

Amino Functionality

At least one entity having been amino-functionalized according to the invention from styrene derivative, dicarboxylic acid and/or diol selectively,
with the equation for the amino-functionality being, irrespective of the entity,

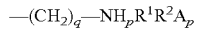

$$-(CH_2)_q-NH_pR^1R^2A_p$$

with
q being either 0, 1 or 2, with q≠0, provided the functionality is bound to an aromatic,
p being 0 or 1,
$R^1$ having been selected from H, linear or branched or cyclic alkyl residues with 1 to 10 carbon atoms,
$R^2$ being a linear or branched or cyclic alkyl residue with 1 to 10 carbon atoms,
A being the anion of an acid, and
the amine nitrogen N of the above formula being neutral (p=0) or positively (p=1) charged.
following neutralization with an acid HA, p can preferably equal 1.
$R^2$ has preferably 1 to 10 carbon atoms, more preferably 3 to 5 carbon atoms.
$R^2$ is preferably branched, in particular selected from isopropyl, tert-butyl or tert-pentyl.
$R^1$ has preferably been selected from H and $R^2$.

If $R^2$ has more than three carbon atoms, $R^1$ is preferably selected from H or an alkyl residue with 1 to 3 carbon atoms.

The acid may be carbonic acid, which is formed from $CO_2$ in the presence of ambient air or water (containing $CO^2$) in situ. In this case there is a mixture of neutralized and not neutralized amine. In the amine neutralized in ambient air or in the presence of water, the counterion A can above all be $HCO_3$. Further neutralization can result from the reaction with COOH groups attached to polymer or oligomer or residual monomer. In this case, counterions can be polymer COO, oligomer COO and residual monomer COO. The addition and use of other mono- or higher functional acids is also possible.

In a preferred embodiment, the styrene derivative has been amino-functionalized. As styrene monomers generally cross-link the unsaturated polyester in a wide range of compositions, the content of amino-functionalized reactive diluents is a particularly effective way of controlling the content of amino-functions in the forming cross-linked plastic.

In an alternative embodiment, the unsaturated polyester (or the diol and/or the dicarboxylic acid) and/or the styrene derivative have been amino-functionalized. Irrespective of the entity, amino-functionality falls under the above-mentioned formula $-(CH_2)_q NH_p R^1 R^2 A_p$, i.e. that the polyester, for example, (or diol and/or dicarboxylic acid) may have a different amino-functionality than the styrene derivative.

Much more preferably, only the styrene derivative has been amino-functionalized.

Amino-Functionalizing of Unsaturated Polyester

Various steps within the raw material or resin production are suitable for functionalizing unsaturated polyester:
   antimicrobial functionalizing of raw material and subsequent condensation of unsaturated polyester. This allows the functionalizing of diol and/or dicarboxylic acid of the unsaturated polyester.
   The unsaturated polyester may be antimicrobially functionalized prior to mixing with the reactive diluent.
   The unsaturated polyester may be antimicrobially functionalized subsequent to complete or partial mixing with the reactive diluent.

The goal of antimicrobial functionalizing is to increase the concentration of antimicrobial functions in the UP thermoset.

The antimicrobially effective amino groups are preferably introduced into certain halogenated or otherwise pre-functionalized diols and/or dicarboxylic acids, which are then used for the production of unsaturated polyester, prior to the production of the unsaturated polyester. One example for this is the synthesis of an amino-functionalized acid component, namely 2,3-bis(tert-butylamino) butanedioic acid from 2,3-dibromobutanedioic acid and tert-butylamine by means of substitution.

Polymer-analogous functionalizing is an alternative to modifying raw materials. Subsequent functionalizing is possible because for the production of polyester, apart from standard components, halogenated diols and dicarboxylic acids can be used without any problems, whose use is state-of-the-art for flame retarded resins. The preferred halogenated raw materials are commercially available representatives, as well as intermediate stages produced by means of bromination. Once the polyester has been produced, it is preferably dissolved in a suitable solvent, and polymer-analogous substitution is carried out using mono- or di-alkylamines. One example for this is the condensation of an unsaturated polyester, whose diol composition contains dibrom-neopentyl glycol in parts. The bromine substitutes introduced in this way can be converted polymer-analogously once the fully condensed polyester has been absorbed in a suitable solvent through substitution with tert-butylamine. The solvent is preferably the reactive diluent.

For unsaturated polyesters, the Michael addition reaction of mono- or di-alkylamines to parts of the fumaric and maleic ester double bond is recommended for the polymer-analogous reaction with the objective of antimicrobial functionalizing. Unsaturated polyesters with a high content of fumaric or maleic ester structure are preferred for this type of functionalizing, and converted between 1 and 80 mol % of the reactive double bond at a relatively low temperature (RT up to 120° C.) with corresponding amines, for example. The remaining reactive double bonds may help radical cross-linking.

In the case of unsaturated polyesters, there is also the possibility of introducing antimicrobially effective amino groups in the form of di-ethoxylated or di-propoxylated mono-alkylamines, which can be used as diol component in unsaturated polyester. Examples are the diols methyl diethanolamine, tert-butyldiethanolamine, methyl diisopropanolamine, tert-butyldiisopropanolamine or N-hydroxyethylpiperazine, bis(2-hydroxyethyl)piperazine, N-hydroxypropylpiperazine, bis-(2-hydroxypropyl)-piperazine or 3-(diethylamino)-1,2-propandiol.

Amino-Functionalized Styrene Derivative

In the composition according to the invention, the styrene derivative has preferably been amino-functionalized. The molecular weight of the amino-functionalized styrene derivative is preferably in the range from 100 to 300 g/mol, in particular in a range from 170 to 250 g/mol. It has been shown that the cross-linking reaction can be incomplete if the molecular weight of the monomer is too high.

The amino-functionalized styrene derivative has preferably 10 to 20 carbon atoms, in particular 12 to 18 carbon atoms.

The amino-functionalized styrene derivative according to the invention has preferably been selected from the group N-(4-ethenylbenzyl)-2-methylpropane-2-amine (also tert-butyl-amino-methyl styrene or TBAMS), N-(4-ethenylbenzyl) ethanamine (also ethyl-aminomethyl-styrene or EAMS), N-(4-ethenylbenzyl)propane-1-amine (also n-propyl-aminomethyl-styrene or PAMS), N-(4-ethenylbenzyl) propane-2-amine (also isopropyl-aminomethyl styrene or IPAMS), N-(4-ethenylbenzyl)butane-1-amine (also n-butyl-aminomethyl-styrene or BAMS), N-(4-ethenylbenzyl)butane-2-amine (also sec-butyl-aminomethyl styrene or SBAMS), N-(4-ethenylbenzyl)-2-methylpropane-1-amine (also isobutyl-Aminomethyl-styrene or IBAMS), N-(4-ethenylbenzyl)pentane-1-amine (also n-pentyl-aminomethyl-styrene or PENAMS), N-(4-ethenylbenzyl)-3-methylbutane-1-amine (also isopentyl-Aminomethyl-styrene or IPENAMS), N-(4-ethenylbenzyl)pentane-3-amine (also 3-pentyl-aminomethyl-styrene or 3-PENAMS), N-(4-ethenylbenzyl)-2-methylbutane-2-amine (also tert-pentyl-aminomethyl-styrene or TPAMS), N-(4-ethenylbenzyl)cyclopentanamine (also cyclopentyl-aminomethyl-styrene or CPENAMS), N-(4-ethenylbenzyl)cyclohexanamine (also cyclohexyl-aminomethyl-styrene or CHAMS), N-(4-ethenylbenzyl)-N,N-dimethylamine (also dimethyl-aminomethyl-styrene or DMAMS, N-(4-ethenylbenzyl)-N,N-diethylamine (also diethyl-aminomethyl-styrene or DEAMS), N-(4-ethenylbenzyl)-N-(propane-2-yl)propane-2-amine (also diisopropyl-aminomethyl-styrene or DIPAMS) and mixtures thereof, with the compounds shown as follows:

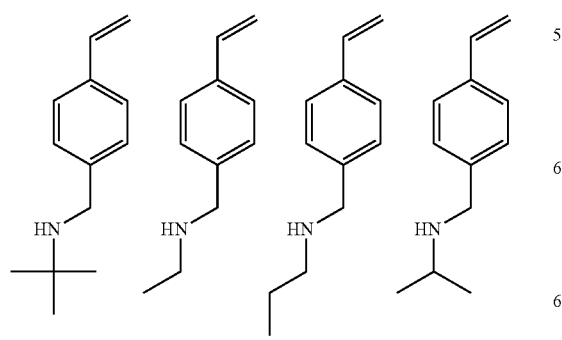

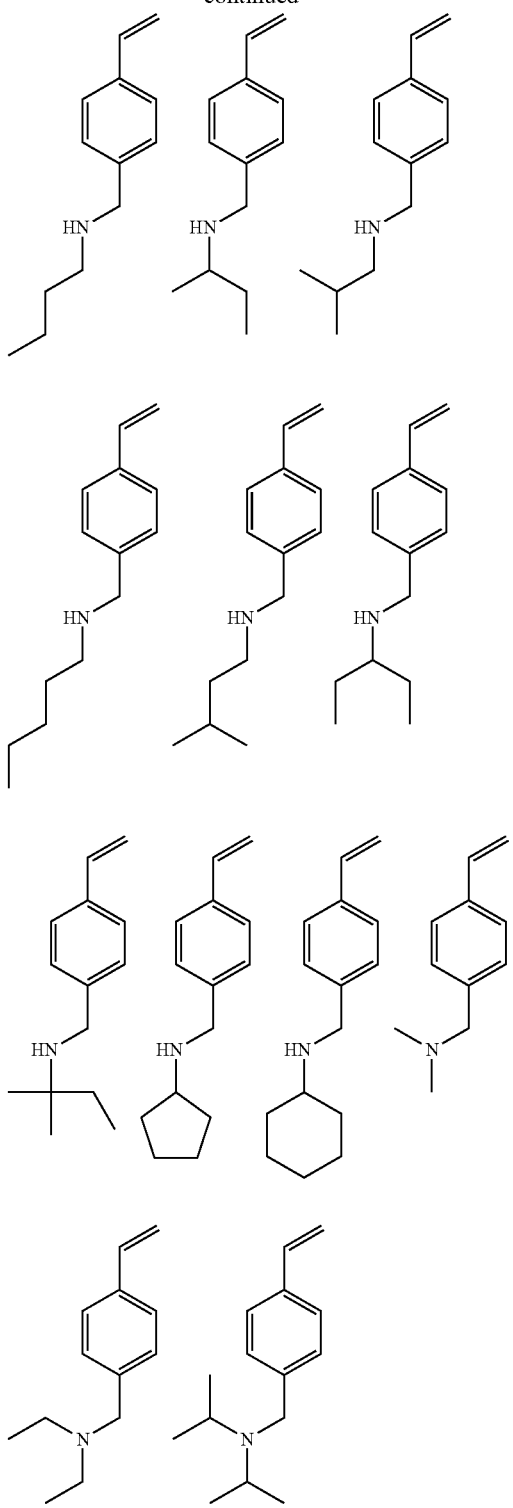

Apart from the mentioned para-isomers, according to the invention all meta-isomers and all ortho-isomers of the mentioned derivatives, as well as any mixture of ortho-, meta- and para-isomers can be used.

In one embodiment, the object underlying the invention is based is solved by using one or a mixture of these three substances

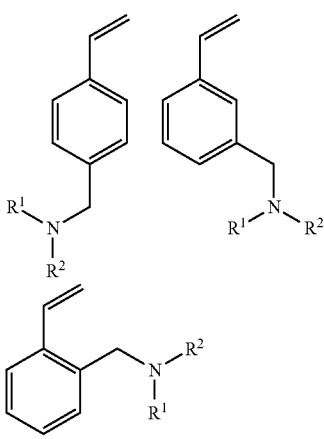

as reactive diluent, whereas $R^1$ and/or $R^2$ have been independently selected from the group methyl, ethyl, n-propyl, iso-propyl, n-butyl, sec-butyl, iso-butyl, tert-butyl, n-pentyl, 3-pentyl, iso-pentyl, tert-pentyl, cyclopentyl, cyclohexyl, whereas $R^1$ can also be H.

During the development of the materials according to the invention, these monomers have been shown to be particularly suitable for the production of antimicrobial materials.

The use of substances with $R^1$ and/or $R^2$ selected from ethyl, isopropyl, tert-butyl, tert-pentyl is particularly preferable, whereas $R^1$ can also be H.

In a particularly preferably embodiment, $R^1$ equals hydrogen and $R^2$ has been selected from isopropyl, tert-butyl, tert-pentyl.

In the present UP resin composition, preferably there are 0.5 to 8 styrene derivative molecules (component b)) per double bond in component a). In other words, the ratio of styrene derivative molecules b) and double bonds from component a) is preferably 0.5:1 to 8:1. The number of styrene derivative molecules/double bonds in component a) is proportional to the respective amounts of substance, so that these amounts can be used as a basis for calculating the above ratio.

The amount of substance of the styrene derivative (component b)) can be determined from the volume used and its molar mass according to $$n_{Sty} = m_{Sty}/M_{Sty}$$

with $m_{Sty}$ describing the volume used and $M_{Sty}$ describing the molar mass of the styrene derivative.

The amount of substance of the double bonds (component a)) can be determined from the volume used and the molar mass of component a) according to $$n_{Dop} = f \cdot m_{Dop}/M_{Dop}$$

with f describing the number of double bonds in one molecule of component a) as well as $m_{Dop}$ describing the volume used and $M_{Dop}$ describing the molar mass of component a).

Composition

The composition contains preferably at least 20% w/w, particularly preferably at least 50% w/w, especially particularly preferably at least 80% w/w of a mixture of components a) and b). Furthermore, the composition may contain, for example, other monomers, oligomers, polymers, light stabilizers, initiators, additives, pigments, separating agents, rheology additives, fibres and/or fillers.

For every 100 weight units of a mixture of components a) and b), the composition should preferably contain 0.2 to 4 weight units of radical initiator. This radical initiator should preferably not be a peroxidic radical initiator. A particular preference is on the radical initiator being a photoinitiator, e.g. a derivative of benzoin, benzil or an alpha-hydroxy ketone or an alpha-amino ketone, an acyl phosphine oxide or a bisacylphosphine oxide. The expert knows a wide range of photoinitiators. Photoinitiators forming C radicals are preferable. C radical generators of the azo initiator type are preferable, such as: 2,2'-azobis(2-methylpropionitrile), also referred to as AIBN, 1,1'-azobis(cyclohexan-1-carbonitrile) or dimethyl-2,2'-azobis(2-methylpropionate) and so-called CC-labile compounds, e.g. 2,3-dimethyl-2,3-diphenylbutane or 3,4-dimethyl-3,4-diphenylhexane.

The radical initiator can also be a mixture of different initiators.

Curing with high-energy radiation, e.g. electron radiation, is also possible.

For every 100 weight units of a mixture of components a) and b), the composition should preferably contain 20 to 280 weight units of filler.

For every 100 weight units of a mixture of components a) and b), the composition should preferably contain 10 to 200 weight units of glass fibre, carbon fibre, aramid fibre, basalt fibre, natural fibre or nonwoven fabric.

Further addition agents, such as light stabilizers, shrinkage-reducing thermoplastic polymers, thickeners, separating agents, skin formers and waxes can be used depending on the process and application.

The resin composition according to the invention, for example subsequent to adding additives, fibres and fillers can be used for the production of sheet moulding compounds (SMC) and bulk moulding compounds (BMC) as well as other compounds.

Use of UP Resins

In another embodiment, the object underlying the invention is based is solved by using the UP resins according to the invention in one of the following processes: Coating, varnishing, casting, dipping, laminating, gap impregnation, centrifuging, gluing, resin injection, pressing, injection moulding, pultrusion, filling and winding.

In another embodiment, the object underlying the invention is based is solved by using the UP resins according to the invention and their composition according to the invention, e.g. in the furniture industry, medical and health care applications, in the medical devices industry, in hospital, doctors' offices, old people's homes, rehabilitation centres, domestic health care and care of the elderly, in the food and meat producing, processing and packaging industry, in the packaging industry, in storage and logistics, in the sealing industry, in animal husbandry and agriculture, in pet care, in the pharmaceutical industry, the domestic appliances industry, in the devices, container and tubing industry, in the electrical, automotive and construction industry, in the aircraft industry, in the textile industry, in the personal hygiene products industry, in the bathroom and kitchen appliances industry, in sports, toy and leisure products, in ship building and watersports, in ventilation and air conditioning, in public, domestic and industrial water supply, in water treatment.

Production of Cured Products

In another embodiment, the object underlying the invention is based is solved by a process for the production of cured products, where the composition according to the invention is cured.

During curing, the temperature should advantageously be set to a range between 20 and 200° C., with lower temperatures being possible if photoinitiators are used.

The cured product, for example a UP thermoset, should preferably be produced using the process according to the invention for the production of cured products. The UP thermoset consists, for example, of a polyester and oligomeric cross-link structures, which have formed from the reactive diluent and which should preferably and predominantly have a medium chain length of 1.5 to 4 monomeric reactive diluent units.

The modulus of elasticity of the UP thermoset should advantageously range between 2,000 and 4,000 N/mm². The UP thermosets should advantageously have an extension in a range between 0.5 and 6%. They are preferably odourless.

The cured polyester resin (UP thermoset) can be fibre reinforced or not fibre reinforced, filled with fillers or not filled with fillers, and irrespective of these aspects it can be used for technical applications of the most diverse types, such as in the food industry, in hospitals or in medical devices, in fridges, cold storage and many other areas. The antimicrobial behaviour is an intrinsic material characteristic and is not caused by conventional, added biocides. This significantly distinguishes the unsaturated polyester resin composition according to the invention and the resulting thermosets and materials from today's state-of-the-art of plastics equipped with biocidal agents, which generally work on the basis of nano silver, isothiazolinones, chlorinated organic compounds, triazine derivatives, copper, tin or arsenic compounds as well as other agents. Due to a (usually slow) release of conventional biocides into the environment, sometimes poor biodegradability, heavy metal contents, possible accumulation in some organisms and/or the distribution and dissemination via the food chain, the use of these conventional biocides is controversial. The new, intrinsically antimicrobial polyester resins reliably avoid these disadvantages.

Product with Antimicrobial Effect

In another embodiment, the object underlying the invention is based is solved by a product with antimicrobial effect containing the cured polyester resin according to the invention.

The product according to the invention consists of more than 20% w/w, preferably more than 50% w/w and particularly preferably of more than 80% w/w of components a) and b).

The product is preferably an adhesive, a sealant, a casting compound, a coating or a mould.

In another embodiment, the object underlying the invention is based is solved by using the UP resins according to the invention for the production of one of the following products:

Furniture and furniture surfaces, adhesives, veneer and paper laminates, buttons, handles, switches and housings, plates, floorings, tubes, profiles, tanks and containers of various types, in particular for drinking water, food and oil, casing of various types, roof coverings, light panels, sealants, putty, Rawlplug filler, polymer concrete, agglo marmor, kitchen sinks, shower basins, bath tubs, washbasins, toilet seats, garden furniture, garden fences, facade plates, cellar window shafts, vehicle parts, lighting support, wind turbines, impregnations, binding agents, casting compounds, filler, and/or reaction mortar, coatings, varnishes, gel coats, top coats, ships, boats, leisure equipment.

Process for the Production of Amino-Functionalized Styrene Derivative

In another embodiment, the object underlying the invention is based is solved by a process for the production of an amino-functionalized styrene derivative, where a) in a first step an aqueous alkali hydroxide solution with a concentration between 3 and 7 mol/l (at least equivalent with the amount of substance of halogen alkyl styrene) is provided,
b) in a second step an amine with at least one hydrogen atom bound to the nitrogen atom is added to the aqueous alkali hydroxide solution,
c) in a third step 0.2 to 0.75 mol equivalent of halogen alkyl styrene in relation to the amount of amine is added,
d) in a fourth step the resulting reaction solution is stirred after adding all of the halogen alkyl styrene, over a period of 4 to 120 hours, and
e) in a fifth step the resulting amino-functionalized styrene derivative is separated from the remaining reaction solution.

The halogen alkyl styrene should preferably be functionalized with the halogen alkyl group on the aromatic ring in ortho and/or meta and/or para position.

The aqueous alkali hydroxide solution is preferably provided at a concentration between 4.5-5.5 mol/l. The alkali hydroxide solution should preferably be a sodium hydroxide solution. The solution should advantageously be at a temperature of 20 to 30° C.

The amine should advantageously have the formula $NHR^1R^2$, with $R^1$ having been selected from H, linear or branched or cyclic alkyl residues with 1 to 10 carbon atoms, and $R^2$ being a linear or branched or cyclic alkyl residue with 1 to 10 carbon atoms.

After completely adding the amine, the reaction solution should preferably be set to a temperature in the range of 60 to 85° C.

In the halogen alkyl styrene, the alkyl group has preferably been substituted with just one halogen atom. The alkyl group is preferably methyl. The halogen atom is preferably chlorine.

The halogen alkyl styrene is preferably added as a solution in tetrahydrofuran.

The concentration of the solution in tetrahydrofuran is preferably between 2 and 3 mol/l. The halogen alkyl styrene is preferably dripped into the existing reaction solution, and the reaction solution is preferably stirred for a period of between 4 and 120 hours. Subsequently, separation is carried out, preferably by vacuum distillation.

Another object of the present invention is a substance selected from

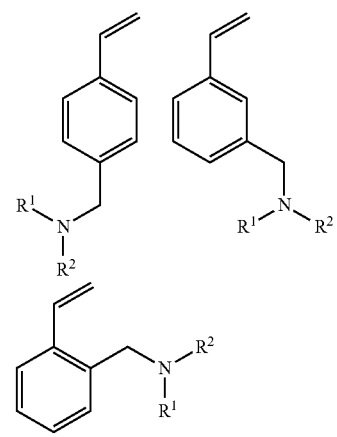

where $R^1$ is hydrogen and $R^2$ is tert-pentyl.

Use of Amino-Functionalized Styrene Derivative

In another embodiment, the object underlying the invention is based is solved by using the amino-functionalized styrene derivative according to the invention for the production of antimicrobial coatings or moulds.

WORKING EXAMPLES

Production of Amino-Functionalized Styrene Derivative (General Provision)

In a 1,000 ml flask, 200 ml of water and 42 g (1.05 mol) of NaOH were added and after complete dissolution, 1.05 mol of the respective amine was added. The flask was heated to a temperature of 60-85° C. while stirring, and over the space of approximately 75 minutes, a solution containing 53.42 g (0.35 mol) of chloromethyl styrene and 150 ml of THF was added dropwise. After completion of the dropwise addition, the reaction flask was left in the oil bath up to a total reaction time of 4-120 hours, stirring continuously, with the reaction time and reaction temperature depending on the amine used. Analysis was carried out using GC-MS. Purification was carried out by means of vacuum distillation.

According to this general provision, amine-functionalized styrene derivative were synthesized using the following amines: tert-butylamine, n-propylamine, isopropylamine, n-butylamine, sec-butylamine, isobutylamine, n-pentylamine, 3-penylamine, isopentylamine, tert-butylamine, cyclopentylamine, cyclohexylamine, diethylamine, diisopropylamine.

The tert-butyl-amino-methyl styrene received with tert-butylamine was abbreviated TBAMS. It was produced at a reaction temperature of 70° C. and a post-stirring time of 24 hours and a conversion rate of >98% and >98% selectivity. Under vacuum distillation, the boiling point of TBAMS was 115° C. at 6 mbar.

Example 1

Condensation of UP 1 ($FS_{1.0}$ $DEG_{0.5}$ $NPG_{0.5}$)

For the production of polyester, 719.63 g of fumaric acid, 329.24 g of diethylene glycol and 322.92 g of neopentyl glycol were weighed into a 2 l four necked flask on a condensation apparatus, and after adding 100 ppm of hydroquinone and 220 ml of water, it was heated up to 80° C. while constantly stirring and under a continuous nitrogen stream (5 l/h). Subsequently, the reaction temperature was increased at a heating rate of approximately 10 K/10 min to 210° C. During constant water separation, the reaction temperature was kept at 210° C. for 2.5 hours. Then, the polyester was cooled down to 115° C. and filled into brown glass bottles.

The acid number established through titration was 28 mg KOH/g UP. The melting viscosity determined with ICI cone plate viscometer was 780 mPas (150° C., 10000 s$^{-1}$).

1A. Resin Production and Curing (2.5 Mol TBAMS Per Mol UP 1 Double Bond)

For the production of the resin, the unsaturated polyester (56.2 g; 28.1 (% w/w) and the amino-functionalized reactive diluent TBAMS (tert-butyl-amino-methyl styrene) (143.8 g; 71.9% w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

The share of polyester corresponds to that of component a) and is 56.2 g (28.1% w/w).

The constitutive repeating unit of the polyester is as follows:

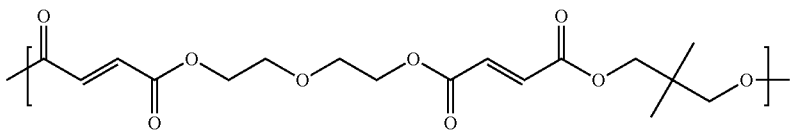

The molar mass of the repeating unit is 370.35 g/mol and contains 2 reactive fumaric acid double bonds.

This results in $n_{Dop}=f \cdot m_{Dop}/M_{Dop}=2 \cdot 56.2$ g/370.35 g/mol=0.303 mol The styrene derivative proportion (tert-butyl-amino-methyl styrene, TBAMS) corresponds to component b) and is 143.8 g (71.9% w/w). The molar mass is 189.3 g/mol.

This results in $n_{Sty}=m_{Sty}/M_{Sty}=143.8$ g/189.3 g/mol=0.760 mol

The ratio of styrene derivative compared with double bonds is:

$$n_{Sty} : n_{Dop} = 0.760 \text{ mol} : 0.303 \text{ mol} = 2.51 : 1$$

1B. Resin Production and Curing (2.25 Mol TBAMS Per Mol UP 1 Double Bond)

For the production of the resin, the unsaturated polyester (45.5 g; 30.3% w/w) and the amino-functionalized reactive diluent TBAMS (tert-butyl-amino-methyl styrene) (104.6 g; 69.7% w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

In this working example, the ratio of styrene derivative compared with double bonds in component a) is 2.25:1.

1C. Resin Production and Curing (2.0 Mol TBAMS Per Mol UP 1 Double Bond)

For the production of the resin, the unsaturated polyester (46.1 g; 32.9% w/w) and the amino-functionalized reactive diluent TBAMS (tert-butyl-amino-methyl styrene) (93.9 g; 67.1% w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

In this working example, the ratio of styrene derivative compared with double bonds in component a) is 2.00:1.

Example 2

Condensation of UP 2 ($FS_{0,5}$ $THPS_{0,5}$ $NPG_{1,0}$)

For the production of polyester, 348.21 g of fumaric acid, 456.45 g of tetrahydrophthalic acid anhydride and 643.65 g of neopentyl glycol were weighed into a 2 l four necked flask on a condensation apparatus, and after adding 200 ppm of hydroquinone, 400 ppm of Fascat 4100 (n-butylstannoic acid) and 170 g of water, it was heated up to 140° C. while constantly stirring and under a continuous nitrogen stream (5 l/h). Subsequently, the reaction temperature was increased at a heating rate of approximately 10 K/30 min to 200° C. During constant water separation, the reaction temperature was maintained for 4 hours, then it was increased to 210° C. and maintained for another 2 hours. After cooling down to 120° C., the polyester was filled into brown glass bottles.

The acid number established through titration was 29.8 mg KOH/g UP. The melting viscosity determined with ICI cone plate viscometer was 770 mPas (150° C., 10000 $s^{-1}$).

2A. Resin Production and Curing (2.5 Mol TBAMS Per Mol UP 2 Double Bond)

For the production of the resin, the unsaturated polyester UP 2 (47.1% w/w) and the amino-functionalized reactive diluent TBAMS (tert-butyl-amino-methyl styrene) (52.9% w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

2B. Resin Production and Curing (2.25 Mol TBAMS Per Mol UP 2 Double Bond)

For the production of the resin, the unsaturated polyester UP 2 (49.8% w/w) and the amino-functionalized reactive diluent TBAMS (tert-butyl-amino-methyl styrene) (50.2% w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

2C. Resin Production and Curing (2.0 Mol TBAMS Per Mol UP 2 Double Bond)

For the production of the resin, the unsaturated polyester UP 2 (52.7% w/w) and the amino-functionalized reactive diluent TBAMS (tert-butyl-amino-methyl styrene) (47.3% w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

Example 3

Condensation of UP-3 ($MSA_{1,0}$ $DEG_{0,5}$ $NPG_{0,5}$)

For the production of polyester, 637.40 g of maleic acid anhydride, 345.18 g of diethylene glycol and 338.54 g of neopentyl glycol were weighed into a 2 l four necked flask on a condensation apparatus, and after adding 100 ppm of hydroquinone, it was heated up to 80° C. while constantly stirring and under a continuous nitrogen stream (5 l/h). Subsequently, the reaction temperature was increased at a heating rate of approximately 10 K/10 min to 200° C. During constant water separation, the reaction temperature was maintained for 3 hours. Then, the polyester was cooled to 115° C. by switching off the heating and it was filled into brown glass bottles.

The acid number established through titration was 29.4 mg KOH/g UP. The melting viscosity determined with ICI cone plate viscometer was 220 mPas (150° C., 10000 $s^{-1}$).

3A. Resin Production and Curing (2.5 Mol TBAMS Per Mol UP 3 Double Bond)

For the production of the resin, the unsaturated polyester UP 3 (28.1% w/w) and the amino-functionalized reactive diluent TBAMS (tert-butyl-amino-methyl styrene) (71.9 w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

3B. Resin Production and Curing (2.0 Mol TBAMS Per Mol UP 3 Double Bond)

For the production of the resin, the unsaturated polyester UP 3 (32.9% w/w) and the amino-functionalized reactive diluent TBAMS (tert-butyl-amino-methyl styrene) (67.1% w/w) were placed on a wagon carriage for 14 days for dissolution and, once they had been fully dissolved, were azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

Example 4

Amino-Functionalizing of UP 3 ($MSA_{1,0}$ $DEG_{0,5}$ $NPG_{0,5}$)

237.10° g of the unsaturated polyester UP 3 was filled into a 1 l flask with reflux condenser and heated to 65° C. While stirring, 11.7 g (corresponds to 12.5 mol % of fumaric and maleic ester units of UP 3) tert-butylamine was added dropwise over a period of 20 minutes, then the temperature was increased step by step to 140° C., and maintained for one hour. Then, the unsaturated polyester was cooled down to 115° C. and filled into brown glass bottles.

Resin Production and Curing

For resin production, 50% w/w of the functionalized, unsaturated polyester UP 3 and 50% w/w of the amino-functionalized reactive diluent TBAMS (tert-butyl-amino-methyl styrene) were filled into a brown glass bottle and placed onto a wagon carriage for dissolution for 14 days. Once it had been fully dissolved, the resin was azo-initiated with 2% w/w of azo initiator V601 [dimethyl 2,2'-azobis(2-methylpropionate)] by Wako. Subsequently, around 8 g each of the transparent, homogeneous resin were placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

Example 5

Condensation of UP 5 ($FS_{1,0}$ $DEG_{3,306}$ $NPG_{0,51}$ $TBBHEA_{0,204}$)

For the production of polyester, 928.56 g of fumaric acid, 259.73 g of diethylene glycol, 424.93 g of neopentyl glycol, 263.14 g of tert-butyl-bis hydroxy-ethylamine (TBBHEA) and 100 g of water were weighed into a 2 l four necked flask on a condensation apparatus, and after adding 200 ppm of hydroquinone, it was heated up to 140° C. while constantly stirring and under a continuous nitrogen stream (20 l/h) over a period of 2 hours, and maintained at 140° C. for 55 minutes under incipient water separation. Subsequently, the reaction temperature was increased at a heating rate of approximately 15 K/10 min to 170° C., kept at 170° C. for approximately 30 minutes and then cooled down to room temperature. On the following day, the reaction mixture was heated uniformly to 185° C. over a period of approximately 210 minutes. Subsequently, the temperature was increased to 190° C. over a period of 20 minutes, and maintained at 190° C. for 90 minutes under further water separation. Then, the polyester was cooled to 115° C. by switching off the heating and it was filled into brown glass bottles.

The acid number established through titration was 34.7 mg KOH/g UP. The melting viscosity determined with ICI cone plate viscometer was 920 mPas (150° C., 1.250 $s^{-1}$).

Resin Production and Curing

For resin production, 51.72 g (40% w/w) of UP 5, 77.58 g (60% w/w) of amino-functionalized reactive diluent TBAMS (tert-butyl-amino-methyl styrene) and 200 ml of acetone were filled into a single neck flask and stirred until the unsaturated polyester had fully dissolved. Subsequently, the acetone was separated in a vacuum using a rotary evaporator. Once the acetone had been separated, 2% w/w of azo initiator V601 [dimethyl 2,2'-azobis(2-methylpropionate)] by Wako was added. After homogenisation of the resin-initiator-mixture, around 8 g each of the mixture was placed on various glass Petri-dishes and cured under nitrogen atmosphere at 70° C. for 2 hours, at 80° C. for 2 hours and at 90° C. for 2 hours.

The resulting, fully cured UP thermoset was tack-free and hard. The UP thermoset was practically odourless and showed excellent antimicrobial characteristics.

Procedure for the Determination of Dynamic-Mechanical Behaviour and Glass Transition Temperature To determine the network-$T_G$, glass fibre-reinforced thermoset test pieces were produced from the resin described in examples 10, 2A, 2C, 3B and 4, and characterized by dynamic mechanical analysis (DMA).

The DMA 242 by Netzsch, which was used here, allows the determination of the storage modulus and the loss modulus, as well as the loss factor of a sample as a function of time and temperature by subjecting it to a sinusidal oscillating force.

The resins produced in the working examples with 2% w/w of initiator (V601 by Wako) were used for the production of the required test pieces.

For this purpose, three 15×15 cm layers of Saertex® glass fibre fabrics (biaxial 0°/90°/type: S14EB540-00620-T1300-487000) impregnated with the respective resin were placed into a 150×150×5 mm sheet form lined with a screwable Mylar® film and freed from air bubbles by pressing down with a spatula. Subsequently, the cavity of the form was fully filled with more resin, covered with Mylar® film and closed by screwing on the top platen. The product was cured in a drying oven for 2 hours at 70, for 2 hours at 80 and for 2 hours at 90° C.

After cooling, the GRP plates were cut using a table circular saw and sanded down to the correct test piece size with a belt if necessary.

Parameters and measurements for the DMA analyses carried out:

Measurements of the test pieces: 50×10×5 mm
Deformation mode: Dual cantilever
Amplitude 30 μm
Dynamic force: 7.55 N
Static force: 4 N
Temperature range: 20-160° C.
Heating rate: 2 K/min
Frequency: 1 Hz/10 Hz
Atmosphere: $N_2$
Flow rate $N_2$: 5 ml/min Procedure for Antimicrobial Tests The method applied is based on the Japanese standard JIS Z 2801:2000. The testing microorganism used in the test was the pathogen *staphylococcus aureus*. A standard pathogen (ATCC 6538), not a multiresistant one, was used.

For each test microbe (here: *staphylococcus aureus*), a germ count specific for the microorganism was set under the conditions used for the production of the initial solution or initial suspension. For *staphylococcus aureus*, the germ count was 108 per ml (see further explanations below).

Antimicrobial activity was determined by comparing the growth of *staphylococcus aureus* on reference surfaces with that on the specimen materials.

The reference material were empty Petri-dishes. The specimens consisted of Petri-dishes, on which a thin layer of polymer had been poured. For each test series, three reference plates were used for the determination of the initial germ count (separate test from the test on antimicrobial behaviour) and three reference plates and three specimen plates were used for the determination of the surface germ count after incubation.

All plates were seeded with 400 µl of *staphylococcus aureus* seeding suspension set to a germ count of $4.0\text{-}10*10^5$ CFU/ml.

The seeding suspension was covered with a sterile PP film to prevent evaporation. Directly following seeding, the three specimen plates and three reference plates were placed into an incubation cabinet and kept there for 2 and 24 hours, respectively, at 35° C. and 90% humidity.

For the determination of the germ count in the seeding solution (initial germ count), three reference plates each were washed out directly after seeding by adding 10 ml SCDLP bouillon medium (soybean casein digest broth with lecithin and polysorbate) to the Petri-dish. The film was turned using a pair of sterile pincers and flooded several times using a 1 ml pipette. The Petri-dish was swirled in a figure-eight motion before 1 ml of the rinsing solution was pipetted in the first dilution step. After preparing the first serial dilution, the germ count was determined using the Drop Plate method. In a dual approach, on a Plate Count (PC) Agar plate, 5 drops of 10 µl each were pipetted into the sector of the respective dilution step using the Drop Plate method. The plates were incubated for 2 hours and 24 hours respectively at 37° C.

Rinsing and determination of germ count on the reference and the specimen plates after incubation was carried out using the same method as the determination of the initial germ count. In addition to raising the detection limit for the sample plates, the germ count of the immediate rinsing solution was determined using the pour plate technique. Again, using a dual approach, 1 ml of the solution each was placed in an empty Petri-dish, and liquid, 45° C. warm, PC agar was poured onto it. By swirling the dish in a figure eight motion, the bacteria were distributed in the agar. The plates were incubated for 48 hours at 37° C.

Following incubation, the colonies in the Petri-dish were counted. The assumption was that each bacteria had grown a visible colony. After incubation, the colonies were visible with the naked eye—a transilluminator could be used to improve visibility.

Based on the volume of the seeding solution and the dilution ratio employed, conclusions could be drawn regarding the living germ count per volume unit (i.e. per ml) of seeding solution. The calculation was based on the weighted arithmetic mean using the following formula:

$$c = \frac{\sum c}{n_1 \cdot 1 + n_2 \cdot 0.1} \cdot d$$

where
$\bar{c}$ represents the weighted arithmetic mean
$\Sigma_c$ represents the total of colonies of all Petri-dishes or sectors included in the calculation
$n_1$ represents the number of Petri-dishes or sectors in the lowest dilution step
$n_2$ represents the number of Petri-dishes or sectors in the next higher dilution step
d represents the factor of lowest evaluated dilution step Using the pour plate technique, Petri-dishes with up to 300 CFU (colony forming units) could be counted. Only plates of up to 150 CFUs per sector could be evaluated using the Drop Plate method.

When determining the germ count per ml, the dilution factor F1 had to be taken into consideration. These led to the total of the volume of SCDLP bouillon and the volume of bacterial suspension on the seeded plate, divided by the volume of bacterial suspension on this seeded plate.

$$F_1 = \frac{10 \text{ ml} + 0.4 \text{ ml}}{0.4 \text{ ml}} = 26$$

$F_1$ Dilution factor of SCDLP bouillon

The following formula resulted for the total germ count on the seeded specimen plates and reference plates, respectively, using the Pour plate technique $$CFU = \frac{\sum c}{n_1 \cdot 1 + n_2 \cdot 0.1} \cdot d \cdot F_1$$

Another dilution factor was relevant for the Drop Plate method, because a quarter of a plate was only seeded with 50 µl, i.e. 0.05 ml. To deduct the germ count per ml from this, 0.05 ml had to be converted to 1 ml, by multiplying by 20.

$$F_2 = 26 \cdot 20$$

$F_2$ Dilution factor to calculate CFU per ml using the Drop Plate method.

The total germ count of the seeded specimen plates and reference plates was calculated taking into consideration all dilution factors according to the following formula:

$$CFU = \frac{\sum c}{n_1 \cdot 1 + n_2 \cdot 0.1} \cdot d \cdot F_2$$

For the calculation of antimicrobial activity, in each test series, the individual results for the germ count per plate were summarized as a simple arithmetic mean as a basis for calculating the $\log_{10}$ reduction factor between sample plate and reference plate.

The calculation was made using the following formula:

$$\log_{10}\text{-reduction} = \log_{10}(kg)_{Ref(x)} - \log_{10}(kg)_{Pr(x)}$$

with
$(kg)_{Ref(x)}$ CFU on the reference plates at the time x and
$(kg)_{Pr(x)}$ CFU on the specimen plates at the time x.

According to JIS Z 2801:2000, antimicrobial activity takes place in a log reduction of at least 0.2 after an incubation period of 24 hours.

In those cases where on the agar plates holding the specimens with the lowest dilution step in the pour plate technique no colonies could be counted, the result was shown as <10 CFU/ml according to the test standard provisions.

Results of the Dynamic Mechanical and the Antimicrobial Tests

| Example | Composition UP | Mass fraction of TBAMS | $T_G$ at 1 HZ | $T_G$ at 10 HZ | Initial germ count (log CFU/ml) | Reference germ count after 2 h (log CFU/ml) |
|---|---|---|---|---|---|---|
| 1A | $FS_{1.0}DEG_{0.5}NPG_{0.5}$ | 0.72 | — | — | 5.7 | 5.5 |
| 1B | $FS_{1.0}DEG_{0.5}NPG_{0.5}$ | 0.70 | — | — | 5.7 | 5.5 |

| | | -continued | | | | |
|---|---|---|---|---|---|---|
| 1C | FS$_{1.0}$DEG$_{0.5}$NPG$_{0.5}$ | 0.67 | 132.4 | 142.6 | 5.7 | 5.5 |
| 2A | FS$_{0.5}$THPSA$_{0.5}$NPG$_{1.0}$ | 0.53 | 98.1 | 106.7 | 5.3 | — |
| 2B | FS$_{0.5}$THPSA$_{0.5}$NPG$_{1.0}$ | 0.50 | — | — | 5.3 | — |
| 2C | FS$_{0.5}$THPSA$_{0.5}$NPG$_{1.0}$ | 0.47 | 95.8 | 103.3 | 5.3 | — |
| 3A | MSA$_{1.0}$DEG$_{0.5}$NPG$_{0.5}$ | 0.72 | — | — | 5.6 | — |
| 3B | MSA$_{1.0}$DEG$_{0.5}$NPG$_{0.5}$ | 0.67 | 110.7 | 118.6 | 5.7 | — |
| 4 | MSA$_{1.0}$DEG$_{0.5}$NPG$_{0.5}$ + TBA | 0.50 | 119.7 | 128.4 | 5.7 | — |
| 5 | FS$_{1.0}$DEG$_{0.3}$NPG$_{0.5}$TBBHEA$_{0.2}$ | 0.60 | 119.3 | 128.9 | 5.7 | — |

| Example | Germ count on specimen surface after 2 h (log CFU/ml) | Log reduction after 2 h | Reference germ count after 24 h (log CFU/ml) | Log reduction after 24 h (log CFU/ml) | Log reduction after 24 h |
|---|---|---|---|---|---|
| 1A | 3.3 | 2.2 | — | — | — |
| 1B | 3.6 | 1.9 | — | — | — |
| 1C | 3.0 | 2.5 | — | — | — |
| 2A | — | — | 8.2 | 1.0 | 7.2 |
| 2B | — | — | 8.2 | 1.0 | 7.2 |
| 2C | — | — | 8.2 | 1.0 | 7.2 |
| 3A | — | — | 7.5 | 1.0 | 6.5 |
| 3B | — | — | 7.8 | 1.0 | 6.8 |
| 4 | — | — | 7.8 | 1.0 | 6.8 |
| 5 | — | — | 7.8 | 1.0 | 6.8 |

Notes:
1. All products showed a marked antimicrobial effectiveness.
2. For some specimens, such as 2A, 2B, 2C, the values for log reduction after 24 hours were identical. This is owed to the fact that the three measurements were carried out in parallel, so that the same reference germ count was used. As the residual germ count of the specimens after 24 hours was always below the method's detection limit, according to the standard it was indicated as log 1, which resulted in identical values for log reduction.

The invention claimed is:

1. An unsaturated polyester resin composition for the production of products with antimicrobial effect containing
   a) an unsaturated polyester from dicarboxylic acid and/or anhydride on the one hand, and diol with a molar ratio of 1.25:1 to 0.75:1 on the other hand, with dicarboxylic acid and/or the anhydride having been at least partially functionalized with a radically reactive double bond, and
   b) styrene derivative as reactive diluent,
   with 0.5 to 8 styrene derivative molecules being present in the composition for each double bond in component a), and
   with at least one entity having been amino-functionalized from styrene derivative, dicarboxylic acid and/or diol selectively,
   with the formula for the amino-functionality being, irrespective of the entity,

   —(CH$_2$)$_q$—NH$_p$R$^1$R$^2$A$_p$ with
   q being either 0, 1 or 2, with q≠0, provided the functionality is bound to an aromatic,
   p being 0 or 1,
   R$^1$ having been selected from H, linear or branched or cyclic alkyl residues with 1 to 10 carbon atoms,
   R$^2$ being a linear or branched or cyclic alkyl residue with 1 to 10 carbon atoms,
   A being the anion of an acid, and
   the amine nitrogen N of the above formula being neutral (p=0) or positively (p=1) charged.

2. Composition according to claim 1, characterised in that the styrene derivative has been amino-functionalized.

3. Composition according to claim 2, characterised in that the amino-functionalized styrene derivative is one of these substances,

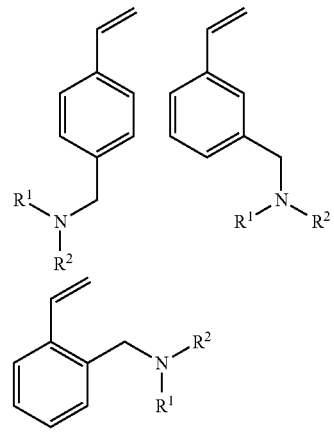

with R$^1$ being a hydrogen, and
R$^2$ having been selected from the group of isopropyl, tert-butyl, tert-pentyl.

4. The composition according to claim 1, characterised in that it contains at least 20% w/w of a mixture of components a) and b).

5. The composition according to claim 1, with 1.5 to 4 styrene derivative molecules being contained in the composition for each double bond in component a).

6. A method of coating, varnishing, casting, dipping, laminating, gap impregnation, spinning, gluing, resin injection, pressing, injection moulding, pultrusion, filling or winding, said method comprising curing the composition of claim 1.

7. Process for the production of cured products, with a composition according to claim 1 being cured.

8. Product with antimicrobial effect containing a cured composition according to claim 7.

9. The product according to claim 8 selected from the following products: furniture and furniture surfaces, adhesives, veneer and paper laminates, buttons, handles, switches and housings, plates, floorings, tubes, profiles, tanks and containers for drinking water, food and oil, casing, roof coverings, light panels, sealants, putty, rawplug filler, polymer concrete, agglo marmor, kitchen sinks, shower basins, bath tubs, wash basins, toilet seats, garden furniture, garden fences, facade plates, cellar window shafts, vehicle parts, lighting support, wind turbines, impregnations, binding agents, casting compounds, filler, and/or reaction mortar, coatings, varnishes, gel coats, top coats, ships, boats or leisure equipment.

10. Process for the production of amino-functionalized styrene derivative, whereas
    a) in a first step an aqueous alkali hydroxide solution with a concentration between 3 and 7 mol/l is provided,
    b) in a second step an half molar equivalent to one molar equivalent amount of amine with at least one hydrogen atom bound to a nitrogen atom is added to the aqueous alkali hydroxide solution,
    c) in a third step 0.2 to 0.5 molar equivalent of halogen alkyl styrene in relation to the amount of alkali hydroxide is added,
    d) in a fourth step the resulting reaction solution is stirred after adding all of the halogen alkyl styrene, over a period of 2 to 48 hours, and
    e) in a fifth step the resulting amino-functionalized styrene derivative is separated from the remaining reaction solution.

11. The composition according to claim 1 where the styrene derivative is selected from

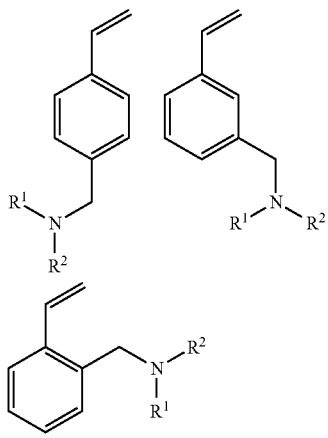

with $R^1$ and/or $R^2$ having been independently selected from the group methyl, ethyl, n-propyl, iso-propyl, n-butyl, sec-butyl, iso-butyl, tert-butyl, n-pentyl, 3-pentyl, iso-pentyl, tert-pentyl, cyclopentyl, cyclohexyl,
whereas $R^1$ can also be H.

12. The composition according to claim 1, characterised in that it contains at least 80% w/w of a mixture of components a) and b).

13. The composition according to claim 2, characterised in that the amino-functionalized styrene derivative has 10 to 20 carbon atoms.

14. The composition according to claim 2, characterised in that the amino-functionalized styrene derivative has 12 to 18 carbon atoms.

15. The composition according to claim 2, wherein that the amino-functionalized styrene derivative is selected from the group consisting of N-(4-ethenylbenzyl)-2-methylpropane-2-amine, tert-butyl-amino-methyl styrene, N-(4-ethenylbenzyl) ethanamine, ethyl-aminomethyl-styrene, N-(4-ethenylbenzyl)propane-1-amine, n-propyl-aminomethyl-styrene, N-(4-ethenylbenzyl)propane-2-amine, isopropyl-aminomethyl styrene, N-(4-ethenylbenzyl)butane-1-amine, n-butyl-aminomethyl-styrene, N-(4-ethenylbenzyl)butane-2-amine, sec-butyl-aminomethyl styrene, N-(4-ethenylbenzyl)-2-methylpropane-1-amine, isobutyl-aminomethyl-styrene, N-(4-ethenylbenzyl)pentane-1-amine, n-pentyl-aminomethyl-styrene, N-(4-ethenylbenzyl)-3-methylbutane-1-amine, isopentyl-aminomethyl-styrene, N-(4-ethenylbenzyl)pentane-3-amine, 3-pentyl-aminomethyl-styrene, N-(4-ethenylbenzyl)-2-methylbutane-2-amine, tert-pentyl-aminomethyl-styrene, N-(4-ethenylbenzyl)cyclopentanamine, cyclopentyl-aminomethyl-styrene, N-(4-ethenylbenzyl)cyclohexanamine, cyclohexyl-aminomethyl-styrene, N-(4-ethenylbenzyl)-N,N-dimethylamine, dimethyl-aminomethyl-styrene, N-(4-ethenylbenzyl)-N,N-diethylamine, diethyl-aminomethyl-styrene, N-(4-ethenylbenzyl)-N-(propane-2-yl)propane-2-amine, diisopropyl-aminomethyl-styrene and mixtures thereof.

* * * * *